US011744786B2

(12) United States Patent
Stern et al.

(10) Patent No.: US 11,744,786 B2
(45) Date of Patent: Sep. 5, 2023

(54) HYGIENE PRODUCT POD AND METHODS OF USING SAME

(71) Applicant: Nohbo, Inc., Palm Bay, FL (US)

(72) Inventors: Benjamin Gabriel Stern, Reston, VA (US); Robert Hutton Ray, Union, IL (US); James J. Ramirez, Palm Bay, FL (US); Matthew Gernstein, Arlington, VA (US)

(73) Assignee: Nohbo, Inc., Palm Bay, FL (US)

( * ) Notice: Subject to any disclaimer, the term of this patent is extended or adjusted under 35 U.S.C. 154(b) by 13 days.

(21) Appl. No.: 16/149,543

(22) Filed: Oct. 2, 2018

(65) Prior Publication Data

US 2019/0216699 A1 Jul. 18, 2019

Related U.S. Application Data

(62) Division of application No. 15/986,592, filed on May 22, 2018, now abandoned.

(60) Provisional application No. 62/618,826, filed on Jan. 18, 2018.

(51) Int. Cl.
*A61K 8/34* (2006.01)
*A61K 8/11* (2006.01)
*A61Q 5/12* (2006.01)
*A61Q 19/10* (2006.01)
*A61Q 5/02* (2006.01)

(52) U.S. Cl.
CPC ............ *A61K 8/345* (2013.01); *A61K 8/11* (2013.01); *A61Q 5/02* (2013.01); *A61Q 5/12* (2013.01); *A61Q 19/10* (2013.01); *A61K 2800/87* (2013.01)

(58) Field of Classification Search
CPC . A61K 8/345; A61K 8/11; A61Q 5/02; A61Q 5/12; A61Q 19/10
See application file for complete search history.

(56) References Cited

U.S. PATENT DOCUMENTS

| | | | |
|---|---|---|---|
| 3,081,267 A | 3/1963 | Laskey et al. | |
| 4,436,789 A | 3/1984 | Davis | |
| 4,996,006 A | 2/1991 | Constantine et al. | |
| 5,062,994 A | 11/1991 | Imperatori | |
| 5,456,863 A * | 10/1995 | Bergmann | A61K 8/416 510/122 |
| 5,756,438 A | 5/1998 | Rau et al. | |
| 5,824,629 A | 10/1998 | Petritsch | |
| 5,840,210 A | 11/1998 | Memula | |
| 5,916,635 A | 6/1999 | Ishii | |
| 5,951,991 A | 9/1999 | Wagner et al. | |
| 5,990,058 A | 11/1999 | Bac et al. | |
| 6,323,307 B1 | 11/2001 | Bigg | |
| 6,566,313 B1 | 5/2003 | Hohenstein | |
| 6,673,765 B1 | 1/2004 | Schulz et al. | |
| 6,753,451 B2 | 6/2004 | Nussbaum et al. | |
| 6,787,512 B1 | 9/2004 | Verrall et al. | |
| 7,115,254 B1 | 10/2006 | Brandt et al. | |
| 7,118,734 B1 | 10/2006 | Fuchshuber et al. | |
| 8,367,048 B2 | 2/2013 | Wells et al. | |
| 8,809,424 B2 | 8/2014 | Feron | |
| 9,393,447 B2 * | 7/2016 | Zasloff | A61Q 19/007 |
| 10,093,827 B2 | 10/2018 | Wolbers | |
| 10,314,935 B2 | 6/2019 | Mcguire, Jr. | |
| 2002/0155962 A1 | 10/2002 | Cincotta et al. | |
| 2002/0198119 A1 | 12/2002 | George | |
| 2003/0054966 A1 | 3/2003 | Bone et al. | |
| 2003/0162841 A1 | 8/2003 | Pathak | |
| 2004/0224863 A1 * | 11/2004 | Sun | A61K 8/42 510/130 |
| 2005/0119151 A1 | 6/2005 | Mayer | |
| 2007/0275064 A1 | 11/2007 | Mumoli | |
| 2008/0145426 A1 | 6/2008 | Amundson et al. | |
| 2008/0152711 A1 | 6/2008 | Mumoli et al. | |
| 2009/0297569 A1 | 12/2009 | Hurwitz | |
| 2010/0313362 A1 | 12/2010 | Vainshelboim | |
| 2010/0316586 A1 | 12/2010 | Knappe et al. | |
| 2011/0081392 A1 | 4/2011 | Arruda et al. | |
| 2011/1088784 | 8/2011 | Denome | |
| 2012/0129955 A1 | 5/2012 | Bernhardt et al. | |
| 2013/0034515 A1 * | 2/2013 | Stone | A61Q 5/12 424/70.122 |
| 2013/0090279 A1 | 4/2013 | Hilvert | |
| 2016/0067155 A1 | 3/2016 | Shimada et al. | |
| 2016/0143833 A1 * | 5/2016 | Jeong | A61K 8/65 424/70.14 |

(Continued)

FOREIGN PATENT DOCUMENTS

CN 105492588 A 4/2016
EP 0896052 A1 10/1999
(Continued)

OTHER PUBLICATIONS

Schulze Zur Wiesche et al., WO 2012/055584, published: May 3, 2012, English machine translation obtained on Nov. 26, 2018.*
Clariant (Product Fact Sheet: Glucotain® Plus, Jan. 2016). (Year: 2016).*
Pazyar et al., "Oatmeal in dermatology: A brief review", Indian Journal of Dermatology, Venereology and Leprology, Mar.-Apr. 2012; vol. 78(2): pp. 142-145.
Notification Concerning Transmittal of International Preliminary Report on Patentability (Chapter 1 of the Patent Cooperation Treaty) for International Application No. PCT/US2016/042572 dated Jan. 25, 2018.

(Continued)

*Primary Examiner* — Genevieve S Alley
(74) *Attorney, Agent, or Firm* — Greenberg Traurig, LLP

(57) ABSTRACT

A hygiene product, a hygiene product pod, and a method of using the hygiene product pod, the hygiene product pod including a water soluble envelope and the hygiene product sealed in the envelope. The hygiene product includes a carrier comprising butylene glycol in an amount ranging from about 40 wt % to about 70 wt %, based on the total weigh of hygiene product, and an active agent including at least one surfactant.

16 Claims, 3 Drawing Sheets

(56) References Cited

U.S. PATENT DOCUMENTS

| | | | |
|---|---|---|---|
| 2016/0317397 | A1 | 11/2016 | Wenz et al. |
| 2017/0259975 | A1 | 9/2017 | Yonezawa |
| 2017/0259976 | A1 | 9/2017 | Lee et al. |
| 2017/0298216 | A1* | 10/2017 | Labeque .................. B65B 1/02 |
| 2018/0000733 | A1 | 1/2018 | Chakroborty |
| 2018/0086523 | A1 | 3/2018 | Ades et al. |
| 2018/0110699 | A1 | 4/2018 | Conway et al. |
| 2018/0110709 | A1 | 4/2018 | Smyth et al. |
| 2018/0311136 | A1 | 11/2018 | Chang et al. |
| 2019/0216698 | A1 | 7/2019 | Stern et al. |

FOREIGN PATENT DOCUMENTS

| | | | |
|---|---|---|---|
| JP | 2002053460 A | | 2/2002 |
| JP | 2009507916 A | | 2/2009 |
| JP | 2010059247 A | | 3/2010 |
| JP | 2012001597 A | | 1/2012 |
| JP | 2012144488 A | | 8/2012 |
| JP | 2013523627 A | | 6/2013 |
| JP | 2015013855 A | | 1/2015 |
| JP | 2016056148 A | | 4/2016 |
| KR | 10-2014-0111903 A | | 9/2014 |
| NL | 148102 A | | 12/1975 |
| WO | 1985002858 A1 | | 7/1985 |
| WO | 93/07245 A2 | | 4/1993 |
| WO | 1997024428 A1 | | 7/1997 |
| WO | 01-01954 A1 | | 1/2001 |
| WO | 02/22091 A1 | | 3/2002 |
| WO | 2004082655 A1 | | 9/2004 |
| WO | 2009153311 A2 | | 12/2009 |
| WO | 2011/094690 A1 | | 8/2011 |
| WO | WO 2012/055584 | * | 5/2012 |
| WO | 2014098268 A1 | | 6/2014 |
| WO | 2015097099 A1 | | 7/2015 |
| WO | 2017011774 A1 | | 1/2017 |
| WO | 2019143809 A1 | | 7/2019 |

OTHER PUBLICATIONS

Gloor et al., "Antiseptic effect of a tropical dermatological formulation that contains Hamamelis distillate and urea", Forsch Komplementarmed Klass Naturheikd, Jun. 2002; 9(3) 153-9. 2 pages.

Notification of Transmittal of International Search Report and Written Opinion for International Application No. PCT/US2016/042572 dated Oct. 21, 2016.

International Search Report and Written Opinion of the International Searching Authority dated Apr. 29, 2019 for International Application No. PCT/US2019/014000, 16 pages.

International Search Report and Written Opinion dated Feb. 8, 2021 for PCT/US2020/059166.

Stepan, Personal Care Sulfate-Free, Jul. 2017 (Year: 2017).

Safety Data Sheet, Colonial Chemical, 2022, Revision No. 1, p. 1-10.

International Search Report and Written Opinion for PCT/US2022/074986, dated Jan. 18, 2023.

Rolling Stone, How this Disruptive Startup Eliminates Plastics Outright from Bathroom, 2022, p. 1-19, downloaded Mar. 17, 2023, https://www.rollingstone.com/culture/culture-news/how-this-disruptive-startup-eliminates-plastics-outright-from-your-daily-routine-1335995/.

Nichol, Luxe Pack LA & MakeUp in LA:Monodose packaging'ssustainable evolution, Luxe Pack LA & MakeUp in LA; 2022, p. 1-6, downloaded Mar. 17, 2023, https://www.luxepackaginginsight.com/article/luxe-pack-la-makeup-in-la-monodose-packaging-s-sustainable-evolution.60347.

Deacetis, Fashion Travel Essentials you Need for 2021, Forbes, 2021, p. 1-10, https://www.forbes.com/sites/josephdeacetis/2021/08/20/fashion-travel-essentials-you-need-for-2021/?sh=473eea9d37de.

Nohbo, 'Shark Tank' Alum Nohbo Raises $3M Series Seed Led By Material Impact, 2020, p. 1-3.

Plastic Generation, Young entrepreneur aims to remove plastic bottles forever!—Plastic Generation, p. 1-10, downloaded Mar. 17, 2023, https://plasticgeneration.com/young-entrepreneur-aims-to-remove-plastic-bottles-forever/.

Neale, 'Shark Tank' shampoo entrepreneur from Viera High guiding Nohbo to new heights, Florida Today, 2020, p. 1-4, downloaded Mar. 17, 2023, https://www.floridatoday.com/story/news/2020/01/10/shark-tank-inventor-viera-high-gets-visit-mark-cuban/4305917002/.

* cited by examiner

HYGIENE PRODUCT POD AND METHODS OF USING SAME

RELATED APPLICATIONS

This application is a division of U.S. patent application Ser. No. 15/986,592, entitled "HYGIENE PRODUCT POD AND METHODS OF USING SAME", filed May 22, 2018, which claims the benefit of priority to U.S. Provisional Application No. 62/618,826, entitled "HYGIENE PRODUCT POD AND METHODS OF USING SAME", filed Jan. 18, 2018, the entire contents of which are incorporated herein by reference.

FIELD

Aspects of the present disclosure provide a hygiene product pod configured for single-use applications, and a method of using such a pod.

BACKGROUND

Hygiene products, such as shampoo, bodywash, shaving cream, and conditioner are usually sold in a liquid or gel format. Such hygiene products generally contain active agents, such as surfactants and/or conditioners, in addition to significant amounts of water and/or viscosity control agents. Such hygiene products are most commonly provided in bottles containing enough product for many applications. While such products are suitable for many consumer applications, there is a need for smaller amounts of hygiene product, particularly in the travel and hospitality industries.

Hygiene products have been provided in small bottles for use in the hospitality and/or travel industries. However, the small bottles of shampoo/conditioner/shaving cream generally found in the hospitality industry have a high packaging to product ratio, which contributes to higher costs and excessive amounts of waste.

In addition, single-dose packages of shampoo/conditioner packaged in plastic sachets, bags, or blister packs have also been developed. However, such packaging is generally not recycled or biodegradable.

SUMMARY

Various embodiments include a hygiene product having a carrier that includes butylene glycol in an amount ranging from about 40 wt % to about 70 wt %, based on the total weigh of hygiene product; and an active agent comprising at least one surfactant.

Various embodiments include a single-use hygiene product pod having a water-soluble envelope and a hygiene product sealed in the envelope, in which the hygiene product includes a carrier comprising butylene glycol in an amount ranging from about 40 wt % to about 70 wt %, based on the total weigh of hygiene product, and an active agent comprising at least one surfactant.

Various embodiments include a method of using a hygiene product pod comprising a water-soluble envelope and a hygiene product sealed in the envelope in which the hygiene product includes an active agent and a carrier comprising butylene glycol in an amount ranging from about 40 wt % to about 70 wt %, based on the total weight of hygiene product, the method including applying water to the pod to dissolve the envelope and release the hygiene product, applying the hygiene product to at least one body part of a user, and rinsing the hygiene product from the body part.

BRIEF DESCRIPTION OF THE DRAWINGS

The accompanying drawings, which are incorporated herein and constitute part of this specification, illustrate exemplary embodiments of the invention, and together with the general description given above and the detailed description given below, serve to explain the features of the invention.

DETAILED DESCRIPTION

Figure 1A:
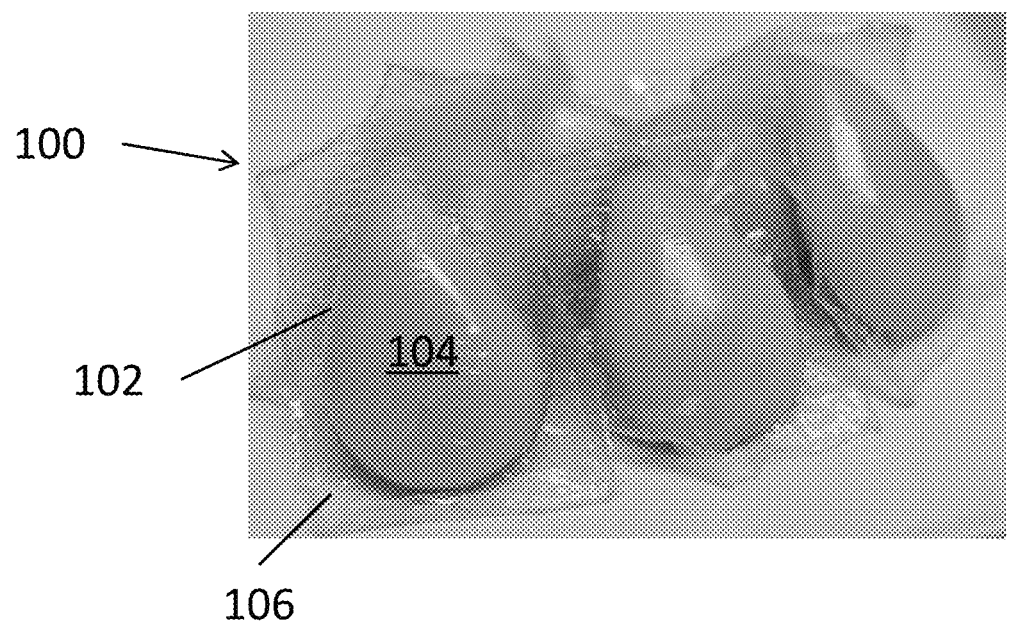
FIG. 1A photograph of the hygiene product pod various embodiments of the present disclosure.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

The word "exemplary" is used herein to mean "serving as an example, instance, or illustration." Any implementation described herein as "exemplary" is not necessarily to be construed as preferred or advantageous over other implementations.

It will also be understood that, as used herein, the terms "the," "a," or "an," mean "at least one," and should not be limited to "only one" unless explicitly indicated to the contrary. Thus, for example, reference to "a slot" includes examples having two or more slots unless the context clearly indicates otherwise.

Ranges can be expressed herein as from "about" one particular value, and/or to "about" another particular value. When such a range is expressed, examples include from the one particular value and/or to the other particular value. Similarly, when values are expressed as approximations, by use of the antecedent "about" or "substantially" it will be understood that the particular value forms another aspect. In some embodiments, a value of "about X" may include values of +/−1% X. It will be further understood that the endpoints of each of the ranges are significant both in relation to the other endpoint, and independently of the other endpoint.

Various embodiments relate to hygiene product pods in which the hygiene product is encapsulated in a water-soluble envelope in a single dose format. The hygiene product pods may provide cleansing and/or conditioning agents for hair and/or skin. In particular, the hygiene product includes an active ingredient, such as shampoo, conditioner, or a combination thereof, within a carrier that features butylene glycol in an amount ranging from about 40 wt % to about 70 wt %, based on the total weigh of hygiene product.

Hygiene Product Pods

Various embodiments include single-dose hygiene products in the form of pods. Herein, the term "pod" refers to water-soluble envelope in the shape of a capsule, sphere, drop, or the like, filled with a hygiene product in which includes an active ingredient within a carrier that is butylene glycol in an amount ranging from about 40 wt % to about 70 wt %, based on the total weigh of hygiene product. For example, a pod may include an envelope encapsulating a liquid or gel of hygiene product. A pod may have any suitable shape and/or size. A pod may contain a sufficient amount of hygiene product for a single use. For example, a pod may contain an amount of shampoo sufficient to clean one head of hair, may contain an amount of bodywash sufficient to wash one body, or may contain an amount of a shaving product sufficient to shave one or more body parts. As used herein, the term "shaving product" may refer to shaving cream, shaving gel, or a precursor composition configured to form a shaving product.

In some embodiments, a pod containing shampoo, conditioner, or shampoo and conditioner within a butylene glycol-based carrier may range in volume from about 4 g to about 12 g, such as from about 5 g to about 8 g. A pod containing bodywash may range in volume from about 6 g to about 15 g, such as from about 8 g to about 10 g. Pods including a concentrated active agent may be smaller than pods containing undiluted or semi-diluted active agents.

Figure 1B:
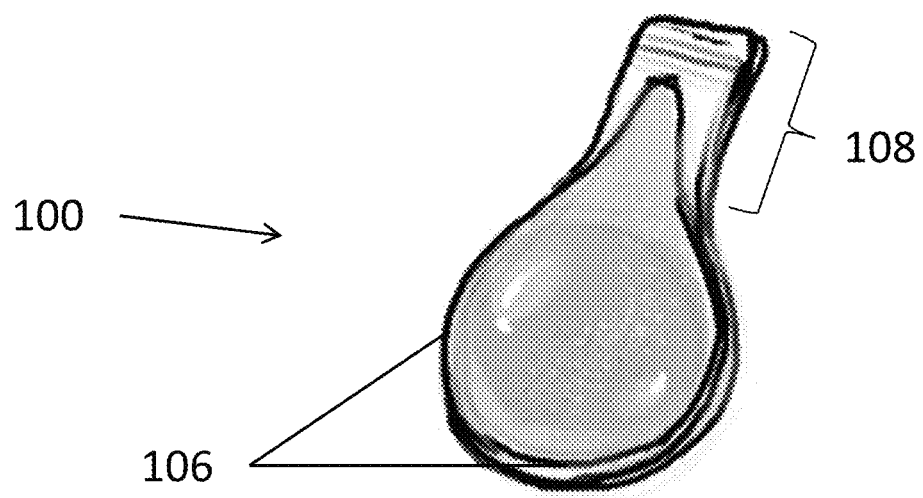
FIG. 1B is a perspective view of the pod of FIG. 1A after an optional cutting process.

FIG. 1A is a photograph of hygiene product pods 100, according to various embodiments. FIG. 1B is a perspective view of the pod 100 of FIG. 1A, after an optional trimming process. Referring to FIGS. 1A and 1B, the pod 100 includes a hygiene product 104 sealed in a water-soluble envelope 102. The pod 100 may be generally drop-shaped (as shown). However, the pod 100 is not limited to any particular shape. For example, the pod 100 may be rectangular, circular, triangular, square, pentagonal, circular, elliptical, tablet-shaped, or the like.

The envelope 102 may be configured to rapidly dissolve in the presence of a solvent such as water. For example, the envelope 102 may include or be formed of a water-soluble material, such as polyvinyl alcohol (PVOH), carboxymethyl cellulose (CMC), or the like. The water-soluble material may be in the form of a film or a woven or non-woven fiber, such as a PVOH or CMC fiber. For example, the envelope 102 may be formed of a PVOH film, such as Monosol 9643, available from Kuraray Inc.

The envelope 102 may have a thickness ranging from about 0.5 mm to about 5.0 mm. The envelope 102 may have a pH ranging from about 4.0 to about 9.0, at a temperature of about 25° C. The envelope 102 may be configured to dissolve in water at about 25° C. in a time period ranging from about 3 seconds to about 15 seconds, such as from about 5 seconds to about 7 seconds.

It has been found that forming the envelope 102 of PVOH may be particularly beneficial. For example, dissolved PVOH may act as a film-former (e.g., conditioning agent) and/or a foam-boosting agent. Accordingly, a PVOH envelope 102 may unexpectedly improve the properties of the hygiene product 104 by adding to suds, bubbles, or foam when in use.

The pod 100 may be formed by sealing two sheets or layers of the water-soluble material around the hygiene product 104. For example, the envelope 102 may be formed by placing the hygiene product 104 between two sheets of the water-soluble material, and then sealing the perimeters of the two sheets so as to form a seal region 106 that extends around the entire perimeter of the pod 100. In some embodiments, the sheets may be partially sealed (e.g., sealed along three sides) to form the envelope 102, after which the hygiene product 104 may be inserted into an open end of the envelope 102 followed by sealing of the open end to complete the pod 100.

In various embodiments, the sealing may be accomplished using any suitable sealing method. In some embodiments, the water-soluble material may be sealed using a heat sealing method. In other embodiments, the sealing may include the use of a water-soluble adhesive. In some embodiments, pods 100 may be formed using a packing machine, such as a Hydroforma packaging machine manufactured by Cloud Packaging Solutions, Des Plaines, Ill.

As shown in FIG. 1B, at least a portion of the seal region 106 may be optionally removed from the pod 100, to form a tab 108. For example, the envelope 102 may be cut during manufacturing of the pod 100. The tab 108 may operate as a contact point to facilitate handling of the pod 100 and/or removal of the pod 100 from product packaging.

In some embodiments, the pod 100 may optionally include an external moisture barrier. For example, the moisture barrier may be a hydrophobic coating or film applied to the outer surface of the envelope 102. In some embodiments, the moisture barrier may comprise hydrophobic esterified plant tri-glycerides, naturally occurring plant fats, or the like. In some embodiments, the moisture barrier may be configured to breakdown or dissolve in warm water.

Figure 2:
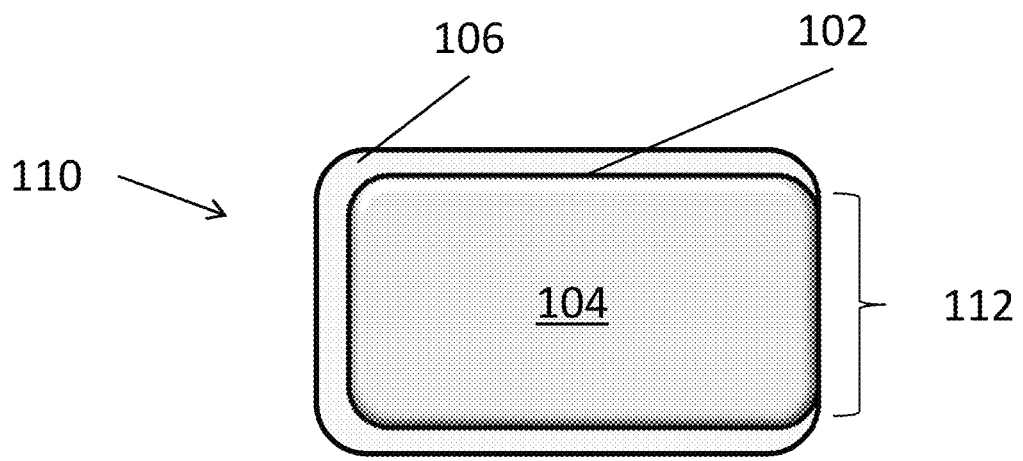
FIG. 2 is a top plan view of a hygiene product pod, according to various embodiments of the present disclosure.

FIG. 2 is a top plan view of a hygiene product pod 110, according to various embodiments. The pod 110 is similar to the pod 100, so only the differences therebetween will be described in detail.

Referring to FIG. 2, the pod 110 includes an envelope 102 in which a hygiene product 104 is disposed. In contrast to the pod 100 illustrated in FIG. 1, the envelope 102 is formed by sealing a single folded sheet of the water-soluble material around the hygiene product 104. As a result, the pod 110 includes a seal region 106 that extends along three sides of the hygiene product 104, and a folded region 112 that extends between opposing ends of the seal region 106.

Figure 3:
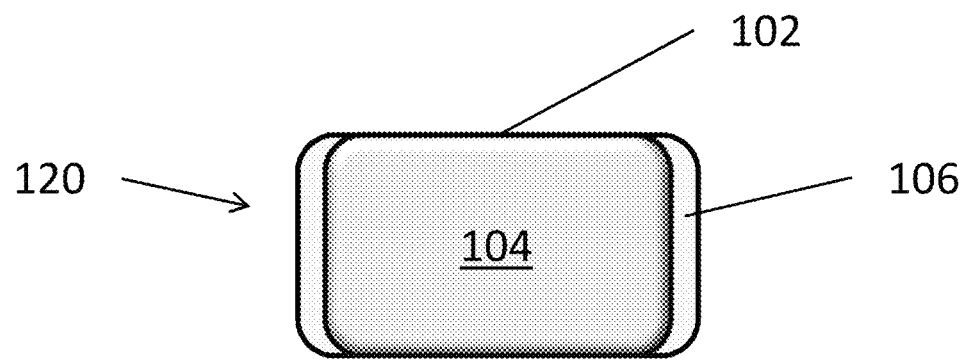
FIG. 3 is a top view of a hygiene product pod, according to various embodiments of the present disclosure.

FIG. 3 is a top view of a hygiene product pod 120 according to various embodiments. The pod 120 is similar to the pod 100, so only the differences therebetween will be described in detail.

Referring to FIG. 3, the pod 120 includes an envelope 102 in which a hygiene product 104 is disposed. In contrast to the pod 100 illustrated in FIG. 1, the envelope 102 is formed by sealing opposing ends of a tubular sheet of the water-soluble material in which the hygiene product 104 is disposed. As a result, the pod 120 includes seal regions 106 disposed at opposing ends of the pod 120.

While three methods of forming pods have been described above, the present disclosure is not limited to any particular method of envelope formation.

Hygiene Products

According to various embodiments, the hygiene product may be in the form of a shampoo, a conditioner, a bodywash, or any combination thereof, such as a combined shampoo, bodywash, and/or conditioner within a carrier that features butylene glycol in an amount ranging from about 25 wt % to about 75 wt %, such as from about 40 wt % to about 70 wt %, based on the total weigh of hygiene product. For example, in some embodiments, the hygiene product may include a carrier comprising butylene glycol in amounts ranging from about 30 wt % to about 70 wt %, from about 35 wt % to about 65 wt %, from about 40 wt % to about 60 wt %, or from about 50 wt % to about 70 wt % based on the total weight of the hygiene product.

For ease of reference, such products may be generically referred to herein as "cleansing products." In some embodiments, the hygiene product may be in liquid or gel form. In other embodiments, the hygiene product may be in the form of a shaving product, such as a shaving gel, cream, liquid, or the like, also within a carrier that features butylene glycol in an amount as described above, such as an amount ranging from about 25 wt % to about 75 wt %, or from about 40 wt % to about 70 wt %, based on the total weigh of hygiene product.

In various embodiments, such as in the case of cleansing products, the hygiene product may include an active agent and a carrier (e.g., a surfactant vehicle or filler) including butylene glycol in an amount ranging from about 25 wt % to about 75 wt %, such as from about 40 wt % to about 70 wt %, based on the total weigh of hygiene product. The active agent may be dispersed in the carrier. The hygiene product may optionally include one or more thickeners (e.g., gellants), and/or one or more secondary ingredients.

In various embodiments, the water content of the hygiene product may be controlled to prevent dissolution of the envelope. For example, the hygiene product may have a free water content of about 20 wt % or less, such as 15% or less, 10% or less, or 5% or less, based on the total weight of the hygiene product. In some embodiments, the hygiene product may have a free water content ranging from about 1% to about 12%, such as from about 2% to about 10%, based on the total weight of the hygiene product. The secondary ingredients may be configured to reduce the water activity (aW) of the hygiene product.

The active agent may include a surfactant and/or a surfactant system comprising a mixture of surfactants, one or more cleansing agents, and/or one or more conditioning agents. The conditioning agents may be configured to counteract the inherent harshness of the surfactants. The conditioning agents, carrier, thickeners (e.g., gellants), and/or secondary ingredients may be configured to increase the integrity of a pod and/or may operate to disperse the active agent when the pod is dissolved in water.

Active Agents

In various embodiments, the active agent may be formulated as a shampoo, a bodywash, a conditioner, or any combinations thereof (e.g., formulated as a 2 in 1 shampoo and conditioner or a 3 in 1 shampoo, conditioner, and bodywash). In other embodiments, the active agent may be formulated as a shaving product. Accordingly, as used herein, the "active agent" may refer to any of the above formulations.

In various embodiments, the active agent may be in the form of a concentrate, such as shampoo concentrate, a conditioner concentrate, a bodywash concentrate, or any combinations thereof. The active agent may be in the form of a shaving product concentrate in other embodiments. In some embodiments, the active agent may include one or more of the above components in a powdered format.

In various embodiments, the active agent may include anionic, nonionic, and/or amphoteric surfactants, or any combinations thereof. Non-limiting examples of suitable anionic surfactants include alkali metal sulforicinates, sulfonated glyceryl esters of fatty acids, such as sulfonated monoglycerides of coconut oil acids, salts of sulfonated monovalent alcohol esters such as sodium oleylisethianate, metal soaps of fatty acids, amides of amino sulfonic acids such as the sodium salt of oleyl methyl tauride, sulfonated products of fatty acids nitriles, such as palmitonitrile sulfonate, sulfonated aromatic hydrocarbons such as sodium alpha-naphthalene monosulfonate, condensation products of naphthalene sulfonic acids with formaldehyde, sodium octahydroanthracene sulfonate, alkali metal alkyl sulfates such as sodium lauryl sulfate, ammonium lauryl sulfate or triethanolamine lauryl sulfate, ether sulfates having alkyl groups of 8 or more carbon atoms, such as sodium lauryl ether sulfate, ammonium lauryl ether sulfate, sodium alkyl aryl ether sulfates, and ammonium alkyl aryl ether sulfates, alkylarylsulfonates having 1 or more alkyl groups of 8 or more carbon atoms, alkylbenzenesulfonic acid alkali metal salts exemplified by hexylbenzenesulfonic acid sodium salt, octylbenzenesulfonic acid sodium salt, calcium salts, decylbenzenesulfonic acid sodium salt, dodecylbenzenesulfonic acid sodium salt, cetylbenzenesulfonic acid sodium salt, and myristylbenzenesulfonic acid sodium salt, sulphuric esters of polyoxyethylene alkyl ether including $CH_3(CH_2)_6CH_2O(C_2H_4O)_2SO_3H$, $CH_3(CH_2)_7CH_2O(C_2H_4O)_{3.5}SO_3H$, $CH_3(CH_2)_8CH_2O(C_2H_4O)_8SO_3H$, $CH_3(CH_2)_{19}CH_2O(C_2H_4O)_4SO_3H$, and $CH_3(CH_2)_{10}CH_2O(C_2H_4O)_6SO_3H$, sodium salts, potassium salts, and amine salts of alkylnapthylsulfonic acid.

Non-limiting examples of suitable cationic surfactants include various fatty acid amines and amides and their derivatives, and the salts of the fatty acid amines and amides. Examples of aliphatic fatty acid amines include dodecylamine acetate, octadecylamine acetate, and acetates of the amines of tallow fatty acids, homologues of aromatic amines having fatty acids such as dodecylanalin, fatty amides derived from aliphatic diamines such as undecylimidazoline, fatty amides derived from aliphatic diamines, such as undecylimidazoline, fatty amides derived from disubstituted amines such as oleylaminodiethylamine, derivatives of ethylene diamine, quaternary ammonium compounds and their salts which are exemplified by tallow trimethyl ammonium chloride, dioctadecyldimethyl ammonium chloride, didodecyldimethyl ammonium chloride, dihexadecyl ammonium chloride, alkyltrimethylammonium hydroxides such as octyltrimethylammonium hydroxide, dodecyltrimethylammonium hydroxide, or hexadecyltrimethylammonium hydroxide, dialkyldimethylammonium hydroxides such as octyldimethylammonium hydroxide, decyldimethylammonium hydroxide, didodecyldimethylammonium hydroxide, dioctadecyldimethylammonium hydroxide, tallow trimethylammonium hydroxide, trimethylammonium hydroxide, methylpolyoxyethylene cocoammonium chloride, and dipalmityl hydroxyethylammonium methosulfate, amide derivatives of amino alcohols such as beta-hydroxylethyl-stearylamide, and amine salts of long chain fatty acids.

Non-limiting examples of suitable cationic surfactants include also quaternary ammonium halides such as octyl trimethyl ammonium chloride, dodecyl trimethyl ammonium chloride, hexadecyl trimethyl ammonium chloride, octyl dimethyl benzyl ammonium chloride, decyl dimethyl benzyl ammonium chloride and coco trimethyl ammonium chloride as well as other salts of these materials, fatty amines and basic pyridinium compounds, quaternary ammonium bases of benzimidazolines, polypropanolpolyethanol amines, polyethoxylated quaternary ammonium salts and ethylene oxide condensation products of the primary fatty amines, available from Armak Company, Chicago, Ill. under the tradenames Ethoquad, Ethomeen, or Arquad. Suitable cationic surfactants can also be an esterquat type compound.

Non-limiting examples of suitable nonionic surfactants include capryloyl/caproyl methyl glucamide and lauroyl/myristoyl methyl glucamide, lauryldimethylamine oxide (e.g., lauramine oxide), decyl glucosides, polyoxyethylene alkyl ethers, polyoxyethylene alkylphenol ethers, polyoxyethylene lauryl ethers, polyoxyethylene sorbitan monoleates, polyoxyethylene alkyl esters, polyoxyethylene sorbitan alkyl esters. Suitable nonionic surfactants include condensates of ethylene oxide with a long chain (fatty) alcohol or (fatty) acid, condensates of ethylene oxide with an amine or an amide, condensation products of ethylene and propylene oxides, fatty acid alkylol amide and fatty amine oxides. Examples of non-ionic surfactants include polyoxyalkylene alkyl ethers such as polyethylene glycol long chain (12-14C) alkyl ether, polyoxyalkylene sorbitan ethers, polyoxyalkylene alkoxylate esters, polyoxyalkylene alkylphenol ethers, ethylene glycol propylene glycol copolymers, polyvinyl alcohol, and alkylpolysaccharides.

Non-limiting examples of suitable amphoteric surfactants include aliphatic secondary or tertiary amine derivatives in which the aliphatic radical is a linear or branched chain containing 8 to 22 carbon atoms and containing-at least one water-soluble anionic group (for example carboxylate, sulphonate, sulphate, phosphate or phosphonate); mention may also be made of $(C_8-C_{20})$alkyl-betaines, sulphobetaines, $(C_8-C_{20})$alkylamido$(C_1-C_6)$alkyl-betaines, or $(C_8-C_{20})$alkylamido$(C_1-C_6)$alkylsulphobetaines. In some embodiments, bocamidopropyl betaine (CAPB) may be included in the hygiene product as an amphoteric surfactant.

In some embodiments, environmentally friendly surfactants may be used, such as sulfate-free surfactants, such as sodium lauryl sulfoacetate, alpha olefin sulfonate, or the like, or combinations thereof.

In some embodiments, surfactants and/or cleansing agents derived from natural oils, such as coconut oil, safflower oil, or the like, may be used. For example, the hygiene product may include a surfactant system comprising a mixture of naturally derived surfactants and/or cleansing agents, such as sodium cocoyl isethionate (Hostapon SCI-85 C, manufactured by Clariant Corp.), cocamidopropyl betaine (Chembetaine C-42, manufactured by Lubrizol Corp.), capryloyl/caproyl methyl glucamide and lauroyl/myristoyl methyl glucamide (GlucoTain Plus, manufactured by Clariant Corp.), cocamidopropyl PG-dimonium chloride phosphate (Cola Lipid C, manufactured by Colonial Chemical Inc.), linoleamidopropyl PG-dimonium chloride phosphate (Cola Lipid SAFL, manufactured by Colonial Chemical Inc.), lauramine oxide (Mackamine LO, manufactured by Solvay Novecare Corp.), or combinations thereof.

In various embodiments, the hygiene product may include, based on the total weight of the hygiene product, from about 20 wt % to about 60 wt %, such as from about 30 wt % to about 50 wt %, from about 35 wt % to about 45 wt %, or about 40 wt % of the surfactant system.

In various embodiments, the surfactant system may include, based on the total weight of the hygiene product, from about 0 wt % to about 40 wt %, such as from about 10 wt % to about 30 wt %, from about 15 wt % to about 27 wt %, from about 18 wt % to about 25 wt %, or from about 20 wt % to about 23 wt % sodium cocoyl isethionate.

The surfactant system may include, based on the total weight of the hygiene product, from about 0 wt % to about 20 wt %, such as from about 1 wt % to about 10 wt %, from about 2 wt % to about 8 wt %, from about 3 wt % to about 7 wt %, or from about 4 wt % to about 6 wt % cocamidopropyl betaine.

The surfactant system may include, based on the total weight of the hygiene product, from about 0 wt % to about 20 wt %, such as from about 2 wt % to about 10 wt %, from about 3 wt % to about 9 wt %, or from about 4 wt % to about 8 wt % capryloyl/caproyl methyl glucamide and lauroyl/myristoyl methyl glucamide.

The surfactant system may include, based on the total weight of the hygiene product, from about 0 wt % to about 12 wt %, such as from about 0.5 wt % to about 6 wt %, from about 1 wt % to about 5 wt %, or from about 2 wt % to about 4% linoleamidopropyl PG-dimonium chloride phosphate.

The surfactant system may include, based on the total weight of the hygiene product, from about 0 wt % to about 12 wt %, such as from about 0.5 wt % to about 6 wt %, from about 1 wt % to about 5 wt %, or from about 2 wt % to about 4% cocamidopropyl PG-dimonium chloride phosphate.

The surfactant system may include, based on the total weight of the hygiene product, from about 0 wt % to about 15 wt %, such as from about 1 wt % to about 5 wt %, from about 2 wt % to about 4 wt %, or from about 3 wt % lauramine oxide.

In some embodiments, the surfactant system may include capryloyl/caproyl methyl glucamide (and) lauroyl/myristoyl methyl glucamide, sodium cocoyl isothionate, cocamidopropyl betaine, and cocamidopropyl PG-dimonium chloride phosphate.

In some embodiments, the active agent may include one or more conditioners. Non-limiting examples of suitable conditioners include petrolatum, fatty acids, esters of fatty acids, fatty alcohols, ethoxylated alcohols, polyol polyesters, glycerin, glycerin mono-esters, glycerin polyesters, epidermal and sebaceous hydrocarbons, lanolin, straight and branched hydrocarbons, silicone oil, silicone gum, vegetable oil, vegetable oil adduct, hydrogenated vegetable oils, non-ionic polymers, natural waxes, synthetic waxes, polyolefinic glycols, polyolefinic monoester, polyolefinic polyesters, cholesterols, cholesterol esters, triglycerides and mixtures thereof.

Carriers

In various embodiments, the carrier may operate as surfactant vehicle and/or filler. In some embodiments, the carrier may be selected or configured to lower the overall reactivity of the hygiene product and the envelope. For example, the carrier may operate to control the free water percentage of the hygiene product. In some embodiments, the carrier may be a non-aqueous liquid and/or may be configured to moisten pod components. In some embodiments, the carrier may also operate as a conditioner for hair and/or skin.

In some embodiments, the carrier may include an organic alcohol, such as, butanediol, propylene glycol, dipropylene glycol, N-acetyl diglycoamine, glycerin (e.g., glycerol), combinations thereof, or the like. With regard to butanediols, 1,3-butylene glycol (e.g., butylene glycol) may be particularly useful as a carrier because butylene glycol has been found by the inventors to be compatible with a hygiene product pod envelope material and to also provide conditioning and/or product feel benefits. However, other butanediols may also be used, such as 1,2-butanediol, 2,3-butanediol, and 1,4-butanediol, either alone or in combination with 1,3-butanediol.

In some embodiments, the hygiene product may include butylene glycol (i.e., 1,3 butanediol) in a range, based on the total weight of the hygiene product, from about 25 wt % to about 75 wt %, such as from about 30 wt % to about 70 wt %, from about 40 wt % to about 70 wt %, from about 35 wt % to about 65 wt %, from about 45 wt % to about 70 wt %, from about 50 wt % to about 70 wt %, or from about 50 wt % to about 60 wt %. In some embodiments, the butylene glycol may be natural butylene glycol, which is derived from plant materials, such as sugar cane. Suitable natural butylene glycol is available from Genomatica Inc.

Thickeners/Gelants

In various embodiments, the hygiene product pods may include one or more thickeners which may be referred to as gellants. For example, the thickeners may include hygroscopic polymers, such as guar gum (e.g., cyamopsis tetragonoloba gum), cationic guar gum, xanthan gum, starch, pregelatinized starch, modified starches, such as hydroxypropyl starch phosphate and sodium starch glycolate, honey, polyvinyl pyrolidone (PVP), ExpertGel EG312 (poloxamer 338/PPG-12/SMDI copolymer) available from DKSH Inc., ExpertGel EG412 (poloxamer 407, PPG-12/SMDI copolymer) available from DKSH Inc, combinations thereof, or the like. In some embodiments, the thickeners may include cellulose derivatives such as carboxymethyl cellulose, cellulose gum, or tylose powder. In some embodiments, the hygiene product may include a polyoxyethylene ether.

In some embodiments, the hygiene product may include a hydroscopic polymer thickener in an amount ranging from about 0 wt % to about 0.4 wt %, such as from about 0.05 wt % to about 0.3 wt %, or from about 0.1 wt % to about 0.2 wt %, based on the total weight of the hygiene product.

For example, the hygiene product may include a modified starch thickener in an amount ranging from about 0.1 wt % to about 3 wt %, such as from about 0.2 wt % to about 2 wt %, or from about 0.3 wt % to about 1 wt %, based on the total weight of the hygiene product.

In some embodiments, the thickeners may include nonionic surfactants configured to form a lamellar network. For example, the thickeners may include a lamellar network formed from polyoxyethylene ethers including a mixture of high molecular mass saturated fatty alcohols, mainly cetyl alcohol and stearyl alcohol, such as ceteareth-20. In some embodiments, the hygiene product may include a nonionic surfactant in an amount ranging from about 8 wt % to about 18 wt %, such as about 12 wt %, based on the total weight of the hygiene product.

Carrier Diffusion Control

In some embodiments, the envelope of the hygiene product pod may have some amount of permeability with respect to the hygiene product. This could lead to diffusion of one or more components of the hygiene product through the envelope over time, which may reduce pod shelf-life. For example, an envelope formed of PVOH could inherently have some amount permeability with respect the butylene glycol carrier. Accordingly, the hygiene product may include thickeners configured to reduce carrier permeation through the envelope.

For example, according to various embodiments, the hygiene product may be configured as a lamellar gellant system. For example, a thickener/gellant may be added to the hygiene product as a secondary ingredient. In some embodiments, a mixture including a nonionic surfactant thickener/gellant, such as a fatty alcohol, an active agent, and a carrier may be heated above the melting point of the surfactant, and then the mixture may be cooled below the melting point of the surfactant. As a result, the surfactant may form a lamellar phase within the carrier.

For example, the mixture may include ceteareth-20, an active agent, and a carrier including butylene glycol. The mixture may be heated to above the melting point of the ceteareth-20 and then cooled, such that the ceteareth-20 forms a lamellar gel network surrounding the butylene glycol.

An amount of nonionic surfactant (e.g., ceteareth-20) included in the hygiene product may range from about 8 wt % to about 18 wt %, such as about 12 wt %, based on the total weight of the hygiene product. Amounts above 18 wt % may excessively reduce foaming after hydration. Amounts of less than about 8 wt % may be insufficient to form a stable gel and reduce diffusion of the butylene glycol. Amounts within the range may provide a flowable, smooth, shampoo or bodywash hygiene product with adequate foaming, and may provide a pod having a shelf life of one year or more.

According to some embodiments, the hygiene product may include an oil phase. For example, oil may be added to an active agent/carrier mixture during or prior to heating the mixture. The heated mixture may be blended to form an oil-in-polyol emulsion, followed by cooling. For example, such an emulsion may include an anhydrous conditioner concentrate as an active agent.

In various embodiments, thickeners such as carboxymethyl cellulose, cellulose gum, or tylose powder may be added to the hygiene product to reduce diffusion of the butylene glycol through the envelope. For example, tylose powder may be added to the hygiene product in an amount ranging from about 0.05 wt % to about 0.5 wt %, such as from about 0.15 wt % to about 0.25 wt %, or about based on the total weight of the hygiene product.

Secondary Ingredients

In various embodiments, the hygiene product pods may include secondary ingredients. For example, the secondary ingredients may include buffers/pH adjusters, dyes/colorants, moisturizers, fragrances, vitamins, texture modifiers, essential oils, foam enhancers, and anti-microbial agents, combinations thereof, or the like. In various embodiments, hygiene products may include from about 0 wt % to about 8 wt % secondary ingredients.

The buffers/pH adjusters may include calcium ions, potassium ions, or hydroxide ions, any combination thereof, or any salts or compounds capable of generation such ions. The buffers/pH adjusters may be blended at various ratios, in order to provide a suitable pH. For example, a suitable amount of buffer/pH adjuster may be added to the hygiene product to provide a slightly acidic pH for compatibility with PVOH envelopes. For example, the hygiene product may advantageously have a room temperature pH ranging from about 4.8 to about 6.9, such as from about 5.0 to about 6.8.

In some embodiments, the secondary ingredients may include essential oils such as lavender oil, rosemary oil, cedar wood oil, thyme oil, peppermint oil, chamomile oil, sage oil, lemon oil, patchouli oil, tea tree oil, ylang ylang oil, vetiver oil, carrot seed oil, cypress oil, helichrysum oil, combinations thereof, or the like.

In some embodiments, hygiene products may include moisturizers such as betaine (Genencare OSMS BA, manufactured by Dupont Corp.) In some embodiments, hygiene products may include vitamins such as tocopherol, DL Panthenol, or combinations thereof.

Secondary ingredients useful for improving dissolvability and/or foaming may include coconut milk powder, arrow root powder, colloidal oatmeal powder, combinations thereof, or the like. In various embodiments, hygiene products may include a secondary ingredient, such as coconut milk powder, arrow root powder, colloidal oatmeal powder, or any combination thereof, in an amount ranging from about 0 wt % to about 22 wt %, such as from about 5 wt % to about 20 wt %, or from about 8 wt % to about 15 wt %. Colloidal oatmeal powder may also operate as a texture modifier to provide a smoother texture.

Any suitable colorant may be used. Hygiene products may include a colorant in an amount ranging from about 0 wt % to about 0.3 wt %, such as from about 0.1 wt % to about 0.2 wt %.

In various embodiments, a suitable fragrance may be used. Useful fragrances may be in liquid form, such as traditional fragrances that are combinations of synthetic and natural compounds, natural fragrances that consist of a blend of natural extracts and essential oils, or essential oils in the pure and neat form. Hygiene products may include a fragrance oil in an amount ranging from about 0 wt % to about 0.3 wt %, such as from about 0.1 wt % to about 0.2 wt %.

In various embodiments, texture modifiers may include micro or macro abrasive agents, such as when a pod includes a body scrub. Suitable abrasive agents include, for example, nut powders, silica powders, polymer beads such as wax beads, combinations thereof, or the like. In some embodiments, hygiene products may include an abrasive agent in an amount ranging from about 0 wt % to about 3 wt %, such as from about 0.1 wt % to about 2 wt %, or from about 0.2 wt % to about 1 wt %.

In some embodiments, texture modifiers may include swellable, cross-linkable, hygroscopic polymers, such as guar gum (e.g., cyamopsis tetragonoloba gum), cationic guar gum, xanthan gum, or the like, or combinations thereof. In some embodiments, hygiene products may include a hygroscopic polymer in an amount ranging from about 0 wt % to about 0.4 wt %, such as from about 0.05 wt % to about 0.3 wt %, or from about 0.1 wt % to about 0.2 wt %.

In various embodiments, anti-microbial agents may be natural materials having anti-microbial effects. For example, anti-microbial agents may include thyme oil, tea tree oil, oregano oil, lavender oil, citrus essential oil, grapefruit seed extract, olive leaf extract, honey, or the like. Hygiene products may include an anti-microbial agent in an amount ranging from about 0 wt % to about 3 wt %, such as from about 0.1 wt % to about 2 wt %, or from about 0.2 wt % to about 1 wt %.

Method of Using Hygiene Product Pods

Figure 4:
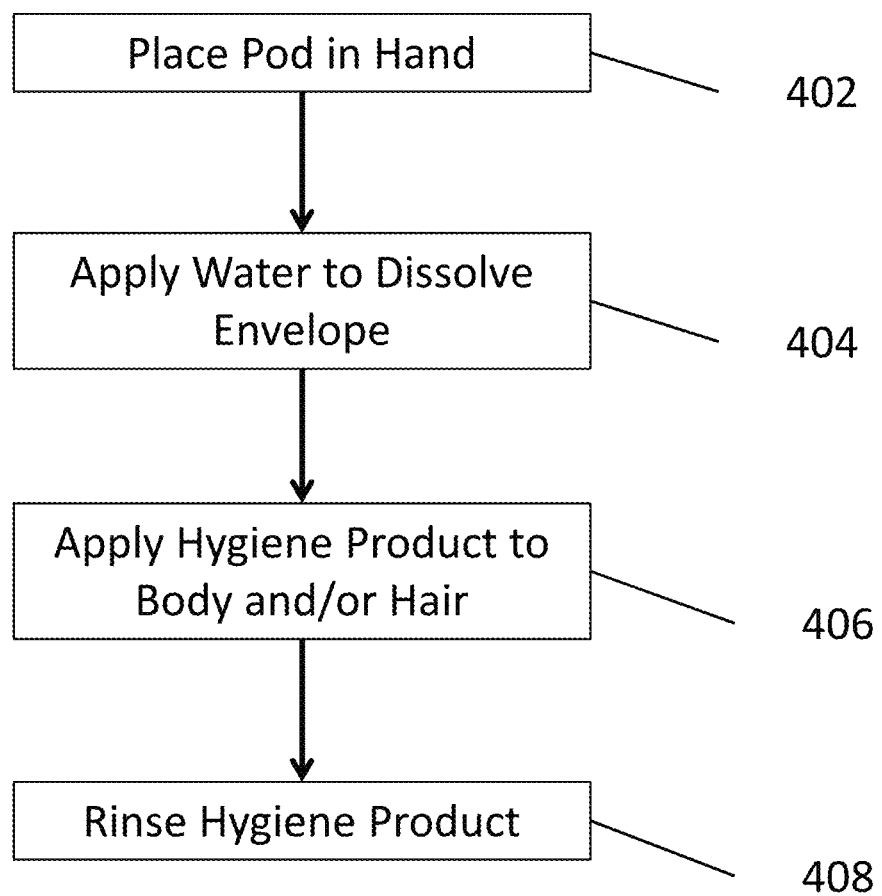
FIG. 4 is a block diagram illustrating a method of using a hygiene product pods, according to various embodiments of the present disclosure.

FIG. 4 is a process flow diagram illustrating a method of using a hygiene product pod according to various embodiments. Referring to FIG. 4, in step 402, a pod as described above may be removed from a container or packaging and may be placed in the hand of a user. The container may include multiple pods and may be configured to limit the exposure of the pods contained therein to moisture. For example, the container may be formed of water resistant paper or paperboard, such as the types of paper used for packaging soap, sugar, or flour. In other embodiments, the pods may be packaged in biodegradable or recyclable packs, for example, in blister packs, polylactic acid bags, for example. Accordingly, the pods may be packaged in a single dose format with minimal environmental impact.

In step 404, water is applied to the pod, such as while holding the pod in one's hands. In some embodiments, friction and/or agitation may also optionally be applied to the pod. The pod may remain in contact with the water in the user's hand and the optional friction may be applied, for a time period sufficient for the water to dissolve the envelope of the pod and release the hygiene product contained therein. For example, a time period for completely or substantially completely dissolving the envelope of the pod may range from about 0.5 seconds to about 1 minute, such as from about 1 second to about 30 seconds, from about 1 second to about 20 seconds, or from about 1 second to about 10 seconds. The dissolution time may vary according to an amount of applied friction and/or the temperature of the applied water (e.g., increased friction and/or water temperatures may result in a reduced dissolution time).

In step 406, the hygiene product is applied to the body of the user. For example, the hygiene product may be applied to the hair of the user, when the hygiene product is in the form of a shampoo and/or a combined shampoo, conditioner, and/or bodywash. In other embodiments, hygiene product may be applied to the body and/or hair of the user, when the hygiene product is in the form of bodywash, a combined shampoo and bodywash, and/or a combined bodywash, shampoo, and conditioner. In other embodiments, the hygiene product may be applied to areas of the user's skin where hair is intended to be removed, when the hygiene produce is in the form of a shaving product.

In step 408, the hygiene product may be rinsed from the applied area or areas.

Exemplary Formulations

Exemplary hygiene product Compositions 1-29 are listed in the following Tables 1-7. The components of each of the example compositions were mixed to form hygiene products. The hygiene products were then packaged to form pods using methods as described above. The pods were then inserted into water-resistant packaging.

TABLE 1

| Component | Comp. 1 Weight % | Comp. 2 Weight % | Comp. 3 Weight % | Comp. 4 Weight % | Comp. 5 Weight % |
|---|---|---|---|---|---|
| 1,3 Butanediol | 70.0 | 60.0 | 60.0 | 68.0 | 62.0 |
| Hostapon SCI-85 P | 22.0 | 22.0 | | | 20.0 |
| Cola Det. EQ-154 | | | 22.0 | 14.0 | |
| Chembetaine C-42 | 3.0 | 6.0 | 6.0 | 6.0 | 5.0 |
| Glucotain Plus | 3.0 | 8.0 | 8.0 | 6.0 | 7.0 |
| Cola Lipid C | 2.0 | 4.0 | 4.0 | | |
| Cola Lipid SAFL | | | | 6.0 | 6.0 |

Composition 1 exhibited immediate phase separation upon mixing. Composition 2 formed an overly dense creamy solid. Compositions 3 and 4 were prepared to test the substitution of replacement of Hostapon SCI-85 P with Cola Det. EQ-154. Compositions 3 and 4 both exhibited phase separation. Composition 5 was a variation of Composition 2, which substituted Cola Lipid SAFL for Cola Lipid C. Composition 5 was dense and creamy and exhibited slight phase separation in air bubbles and crevices of retain.

TABLE 2

| Component | Comp. 6 Weight % | Comp. 7 Weight % | Comp. 8 Weight % | Comp. 9 Weight % | Comp. 10 Weight % |
|---|---|---|---|---|---|
| 1,3 Butanediol | 62.0 | 62.0 | 50.0 | 60.0 | 59.0 |
| Hostapon SCI-85 P | 20.0 | 20.0 | 21.0 | 21.0 | 21.0 |
| Chembetaine C-42 | 5.0 | 5.0 | | | |
| Glucotain Plus | 6.0 | 6.0 | 8.0 | 4.0 | 7.0 |
| Cola Lipid C | | | 4.0 | 2.0 | |
| Cola Lipid SAFL | 4.0 | 4.0 | | 2.0 | 5.0 |
| Mackomine LO | | | 4.0 | 3.0 | |
| Chembetaine C-42 | | | 6.0 | 4.0 | 5.0 |
| Glycerin | | | 3.0 | 2.5 | |
| Water | | | 4.0 | | |
| Essential Oil Blend | | | | 1.5 | |
| Merquat 3330PR | 3.0 | | | | |
| Genencare OSMS | | 3.0 | | | 3.0 |

Compositions 6-13 included conditioning agents and essential oils, as well as additional ingredients, to produce stable, dense hygiene products. In Composition 6, Merquat 3330 PR was initially mixed with butylene glycol and quickly polymerized to form a globule that would not associate with the remaining components. Composition 7 exhibited phase separation at the bottom of the sample. Composition 8 included an additional foam booster and water in an attempt to partially hydrate the Hostapon SCI-85 P. Composition 8 formed a thick paste. Composition 9 formed a softer, creamier hygiene product than previous compositions. Composition 10 formed a relatively soft and creamy hygiene product paste, but was not flowable and exhibited some phase separation.

TABLE 3

| Component | Comp. 11 Weight % | Comp. 12 Weight % | Comp. 13 Weight % | Comp. 14 Weight % | Comp. 15 Weight % |
|---|---|---|---|---|---|
| 1,3 Butanediol | 59.0 | 58.0 | 59.0 | 61.0 | 59.0 |
| Hostapon SCI-85 P | 21.0 | 13.0 | 19.5 | 19.5 | 19.5 |
| GlucoTain Plus | 8.0 | 7.0 | 8.0 | 7.0 | 8.0 |
| Cola Lipid C | | 5.0 | | | |
| Cola Lipid SAFL | 6.0 | | 6.0 | 6.0 | 6.0 |
| Chembetaine C-42 | 6.0 | 5.0 | 6.0 | 6.0 | 6.0 |
| Essential Oil Blend | | 1.5 | 1.5 | 1.5 | 1.5 |
| Genencare OSMS BA | | 1.0 | | 1.0 | |
| Arnica Extract | | | | 1.5 | |
| Poly Sugamulse | | | | 3.0 | |
| Tocopherol | | | | 0.5 | |
| Water | | 7.5 | | | |

Composition 11 formed a relatively soft and creamy paste that was not flowable. Composition 12 formed a spongy solid. Composition 13 was spreadable and soft and exhibited high stability. Composition 14 tested the inclusion of arnica extract and Poly Sugamulse as an emulsifier, which resulted in a granular paste. Composition 15 was similar to Composition 5, but included an increased liquid to surfactant ratio.

TABLE 4

| Component | Comp. 16 Weight % | Comp. 17 Weight % | Comp. 18 Weight % | Comp. 19 Weight % | Comp. 20 Weight % |
|---|---|---|---|---|---|
| 1,3 Butanediol | 60.0 | 59.0 | 59.0 | 69.5 | 60.9 |
| Hostapon SCI-85 P | 18.5 | 18.5 | 17.0 | 14.0 | 18.0 |
| GlucoTain Plus | 7.0 | 7.0 | 6.0 | 3.0 | 7.0 |
| Chembetaine C-42 | 6.0 | 6.0 | 5.0 | 3.0 | 5.0 |
| Cola Lipid C | | | | 4.0 | |
| Cola Lipid SAFL | 6.0 | 6.0 | 5.0 | 2.0 | 5.0 |
| Essential Oil Blend | | 1.5 | 1.5 | 1.5 | 1.5 |
| Arnica Extract | | 1.0 | 2.0 | 2.0 | 0.5 |
| Genencare OSMS BA | 0.5 | 0.5 | | | |
| DL Panthenol | 0.5 | 0.5 | 1.0 | 1.0 | 0.5 |
| Coconut Milk Powder | | | 3.0 | | 1.5 |
| Tocopherol | | | 0.5 | | 0.1 |

Compositions 16-22 were formulated to provide lower viscosity hygiene products. Compositions 16 and 17 were warmed during mixing to facilitate dissolution of the Genencare and Panthenol conditioners. Composition 18 exhibited relatively lower viscosity but also exhibited slight phase separation after 48 hours. Composition 19 had even lower viscosity but also exhibited increased phase separation. Composition 20 was formulated to correct the deficiencies of Composition 19, but resulted in a hygiene product that was overly viscus (hard).

TABLE 5

| Component | Comp. 21 Weight % | Comp. 22 Weight % |
|---|---|---|
| 1,3 Butanediol | 60.9 | 20.9 |
| Propane-1,2-Diol | | 40.0 |
| Hostapon SCI-85 P | 18.0 | 18.0 |
| GlucoTain Plus | 7.0 | 7.0 |
| Chembetaine C-42 | 5.0 | 5.0 |
| Cola Lipid SAFL | 5.0 | 5.0 |
| Essential Oil Blend | 1.5 | 1.5 |
| Arnica Extract | 0.5 | 0.5 |
| Coconut Milk Powder | 1.5 | 1.5 |
| DL Panthenol | | |
| Genencare OSMS BA | 0.5 | 0.5 |
| Tocopherol | 0.1 | 0.1 |

Composition 21 was similar to Composition 20, except for substituting Genencar for Panthenol, resulting in improved flowability, stability, and texture. Composition 22 included both butylene glycol and propylene glycol, resulting in a composition that dissolved a PVOH envelope when inserted therein.

TABLE 6

| Component | Comp. 23 Weight % | Comp. 24 Weight % | Comp. 25 Weight % | Comp. 26 Weight % |
|---|---|---|---|---|
| 1,3 Butanediol | 51.0 | 48.4 | 51.3 | 51.2 |
| Ceteareth-20 | 12.0 | 14.0 | 10.0 | 12.0 |
| Hostapon SCI-85 P | 21.0 | 23.0 | 21.0 | 21.0 |
| GlucoTain Plus | 5.0 | 4.0 | 5.0 | 5.0 |
| Cola Lipid SAFL | 4.0 | 3.0 | 2.0 | 2.0 |
| Cola Lipid C | 3.0 | 3.0 | 4.0 | 4.0 |
| Chembetaine C-42 | 2.0 | 1.0 | 3.0 | 3.0 |
| Essential Oil Blend | 1.4 | 1.5 | 1.5 | 1.5 |
| Arnica Extract | 0.5 | 0.5 | 0.1 | 0.1 |
| Coconut Milk Powder | | | 1.5 | 2.0 | 0.1 |
| Tocopherol | 0.1 | 0.1 | 0.1 | 0.1 |

Compositions 23-26 were formulated to reduce diffusion of the butylene glycol through the PVOH envelope. Compositions 23-26 were formed by dissolving Ceteareth-20 in butylene glycol, while heating above the melting point of Ceteareth-20. The mixtures were cooled to form a lamellar network surrounding the butylene glycol, SCI was added, and then the remaining components were added to form hygiene products.

Composition 23 exhibited moderate gelation and no syneresis. Composition 24 exhibited stable gelation, but poor performance due to excessive Ceteareth-20 emulsification. Composition 25 exhibited moderate gelation, but exhibited phase separation of SCI powder at the bottom of the sample. Composition 26 exhibited improved gelation compared to Composition 25, but also exhibited phase separation of SCI powder.

TABLE 7

| Component | Comp. 27 Weight % | Comp. 28 Weight % | Comp. 29 Weight % |
|---|---|---|---|
| 1,3 Butanediol | 59.5 | 59.35 | 59.25 |
| Tylose Powder | 0.5 | 0.25 | 0.15 |
| Hostapon SCI-85 P | 21.0 | 21.0 | 21.0 |
| GlucoTain Plus | 5.0 | 5.0 | 5.0 |
| Cola Lipid SAFL | 4.0 | 4.0 | 4.0 |
| Cola Lipid C | 4.0 | 4.0 | 4.0 |
| Chembetaine C-42 | 3.5 | 3.5 | 3.5 |
| Essential Oil Blend | 1.5 | 1.5 | 1.5 |
| Genencare OSMS BA | 0.5 | 0.5 | 0.5 |
| Arnica Extract | 0.1 | 0.5 | 0.5 |
| Coconut Milk Powder | 0.2 | 0.2 | 0.2 |
| Extracts | 0.1 | 0.1 | 0.3 |
| Tocopherol | 0.1 | 0.1 | 0.1 |

Compositions 27-29 utilized Tylose powder as a gellant to prevent butylene glycol diffusion. Compositions 27-29 were formed by dissolving Tylose in butylene glycol, while heating at about 60° C. The mixtures were cooled and the remaining components were then added. Composition 27 exhibited good stability, but was overly viscus and included undispersed Tylose powder. Composition 28 exhibited good stability, reduced viscosity, as compared to Composition 27. Composition 29 produced a free-flowing gel having good stability and viscosity. Compositions 27-29 were all highly compatible with PVOH envelopes.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the scope of the invention. Thus, the present invention is not intended to be limited to the aspects and/or embodiments shown herein but is to be accorded the widest scope consistent with the following claims and the principles and novel features disclosed herein.

What is claimed is:

1. A method comprising: contacting a hygiene product pod comprising a water-soluble envelope and a liquid hygiene product encapsulated within the water-soluble envelope with an amount of water sufficient to dissolve the water-soluble envelope and release the liquid hygiene product, wherein the liquid hygiene product is a shampoo, bodywash, conditioner, or any combination thereof, and wherein the liquid hygiene product comprises:
   (a) a glycol carrier, wherein the glycol carrier comprises at least one of: a butylene glycol, a propylene glycol, dipropylene glycol; or N-acetyl diglycoamine;
   (b) a plurality of non-ionic surfactants in a combined amount of from about 2 wt % to about 12 wt %, based on the total weight of the liquid hygiene product, wherein the plurality of non-ionic surfactants comprises capryloyl methyl glucamide, caproyl methyl glucamide, lauroyl methyl glucamide, and myristoyl methyl glucamide; and
   (c) a cationic surfactant in an amount of from about 1 wt % to about 12 wt %, based on the total weight of the liquid hygiene product, wherein the cationic surfactant comprises linoleamidopropyl PG-dimonium chloride phosphate;
      wherein the liquid hygiene product does not dissolve the water-soluble envelope when encapsulated in the water-soluble envelope, and wherein the liquid hygiene product does not phase separate within the water-soluble envelope.

2. The method of claim 1, wherein the liquid hygiene product further comprises at least one anionic surfactant.

3. The method of claim 1, wherein the liquid hygiene product further comprises at least one amphoteric surfactant.

4. The method of claim 3, wherein the at least one amphoteric surfactant is cocamidopropyl betaine.

5. The method of claim 4, wherein the cocamidopropyl betaine is present in an amount of from about 1 wt % to about 10 wt %, based on the total weight of the liquid hygiene product.

6. The method of claim 4, wherein the cocamidopropyl betaine is present in an amount of from about 4 wt % to about 6 wt %, based on the total weight of the liquid hygiene product.

7. The method of claim 1, wherein the water-soluble envelope dissolves in the amount of water at a temperature of about 25° C. in a time period of from about 3 seconds to about 15 seconds.

8. The method of claim 1, wherein the liquid hygiene product further comprises a quaternary ammonium salt.

9. The method of claim 1, wherein the liquid hygiene product further comprises an additional non-ionic surfactant.

10. The method of claim 1, wherein the glycol carrier comprises the butylene glycol, wherein the butylene glycol comprises 1,2-butanediol, 1,3-butanediol, 2,3-butanediol, or 1,4-butanediol.

11. The method of claim 1, wherein the glycol carrier is in an amount that comprises about 21 wt %, based on the total weight of the liquid hygiene product.

12. The method of claim 1, wherein the linoleamidopropyl PG-dimonium chloride phosphate is present in an amount of about 5 wt %, based on the total weight of the liquid hygiene product.

13. The method of claim 1, wherein the liquid hygiene product further comprises lauramine oxide.

14. The method of claim 1, wherein the liquid hygiene product further comprises cetyl alcohol.

15. The method of claim 1, wherein the liquid hygiene product further comprises stearyl alcohol.

16. The method of claim 1, wherein the liquid hygiene product comprises a free water content of about 20 wt % or less, based on the total weight of the liquid hygiene product.

* * * * *